United States Patent [19]

Gieske et al.

[11] 4,051,234

[45] Sept. 27, 1977

[54] ORAL COMPOSITIONS FOR PLAQUE, CARIES, AND CALCULUS RETARDATION WITH REDUCED STAINING TENDENCIES

[75] Inventors: Henry Anthony Gieske, Covington, Ky.; Prem Sagar Juneja, Cincinnati, Ohio

[73] Assignee: The Procter & Gamble Company, Cincinnati, Ohio

[21] Appl. No.: 681,867

[22] Filed: Apr. 29, 1976

Related U.S. Application Data

[63] Continuation-in-part of Ser. No. 584,304, June 6, 1975, abandoned, which is a continuation-in-part of Ser. No. 495,951, Aug. 9, 1974, abandoned.

[51] Int. Cl.$^2$ .......................... A61K 7/18; A61K 7/22
[52] U.S. Cl. .......................................... 424/52; 424/54
[58] Field of Search ..................................... 424/49–58

[56] References Cited

U.S. PATENT DOCUMENTS

| | | | |
|---|---|---|---|
| 2,975,102 | 3/1961 | Matsumura et al. | 424/49 |
| 3,934,002 | 1/1976 | Haefele | 424/54 |
| 3,937,805 | 2/1976 | Harrison | 424/52 |
| 3,937,807 | 2/1976 | Haefele | 424/52 |

FOREIGN PATENT DOCUMENTS

| | | |
|---|---|---|
| 2,223,766 | 12/1972 | Germany |
| 825,577 | 12/1959 | United Kingdom |
| 1,381,361 | 1/1975 | United Kingdom |
| 490,384 | 2/1937 | United Kingdom |

*Primary Examiner*—Shep K. Rose
*Attorney, Agent, or Firm*—Ronald L. Hemingway; George W. Allen; Richard C. Witte

[57] ABSTRACT

Oral compositions such as toothpastes, mouthwashes and the like containing a particular substantive bis-biguanide compound which inhibits the formation of plaque and caries, an a specific amino carboxylate compound which inhibits the tendency of the bis-biguanide compound to produce a stain on oral surfaces, preferably while maintaining the bis-biguanide as a water-soluble salt.

20 Claims, No Drawings

ORAL COMPOSITIONS FOR PLAQUE, CARIES, AND CALCULUS RETARDATION WITH REDUCED STAINING TENDENCIES

CROSS-REFERENCE TO RELATED APPLICATIONS

This application is a continuation-in-part of abandoned application Ser. No. 584,304, filed June 6, 1975 which is in turn a continuation-in-part of abandoned application Ser. No. 495,951, filed Aug. 9, 1974 abandoned.

BACKGROUND OF THE INVENTION

The field of this invention is "oral compositions" which term is used herein to designate products which in the ordinary course of usage are retained in the oral cavity for a time and in a manner sufficient to contact essentially all of the dental surfaces, but are not intentionally ingested. Such products include, for example, dentifrices, mouthwashes, prophylaxis pastes and topical solutions.

The bis-biguanide compounds of this invention are known, having been disclosed in U.S. Pat. No. 2,684,924, Rose et al., patented July 27, 1954; U.S. Pat. No. 2,990,425, Senior et al., patented June 27, 1961; U.S. Pat. No. 2,830,006, Burtwell et al, patented Apr. 8, 1958; U.S. Pat. No. 2,863,919, Burtwell et al., patented Dec. 9, 1958, and Kemanord; Netherlands application 72/06762, published Nov. 21, 1972 (Corresponds to British Pat. No. 1,381,361, published Jan. 22, 1975).

Attempts have been made in the prior art to reduce the tooth-staining tendency of bis-biguanide antiplaque agents. For example Haefele, U.S. Pat. No. 3,934,002 issued Jan. 20, 1976 and Haefele's pending U.S. pat. application Ser. No. 635,030, filed Nov. 25, 1975, relate to the formation of insoluble bis-biguanide salts to reduce staining of teeth. Such insoluble materials are not, however, very useful in formulating clear liquid oral products such as mouthwashes and gel toothpastes.

It is also possible to reduce the tooth staining tendency of bis-biguanides by combining them with metal chelating agents. For example, Haefele, U.S. Pat. No. 3,937,807, issued Feb. 10, 1976 discloses the combination of bis-biguanides with certain amino carboxylate compounds. Furthermore, our concurrently filed copending application having Ser. No. 681,868 (continuation-in-part of Ser. No. 652,692, filed Jan. 27, 1976 and its parent applications) disclose that particular chelating agents are effective in reducing staining by the bis-biguanides, without the formation of insoluable salts. Care must be taken, however, in selecting chelating agents for use in oral compositions since some chelators have a tendency to damage dental enamel. There is thus a continuing need for reduced staining bis-biguanide compositions which contain soluble materials and which do not contain chelating agents that are potentially damaging to teeth.

Accordingly, it is an object of the present invention to provide antiplaque compositions and methods which employ bis-biguanides but which produce little or no stain on dental surfaces.

It is a further object of the present invention to provide reduced staining anti-plaque compositions and methods which utilize water soluble materials.

It is a further object of the present invention to provide reduced staining antiplaque compositions and methods which employ materials that are chemically compatible with dental enamel.

It has been discovered that by combining bisbiguanide antiplaque agents and chelating agents such as ethylenediamine diacetic acids and salts, the above objectives can be realized and reduced staining, antiplaque compositions and methods can be provided which are unexpectedly superior to similar compositions and methods of the prior art.

SUMMARY OF THE INVENTION

It has now been discovered that if the specific bisbiguanide compounds disclosed herein and the specific amino carboxylate compounds disclosed herein are used together in the oral cavity in the concentrations set forth herein, with the amino carboxylate compound in a molar excess as set forth hereinafter, and the compounds either being used together or sequentially, the stain that is normally caused by continuous use of the bis-biguanide compounds alone is effectively reduced. It is preferred that the amino carboxylate compound and the bis-biguanide compound be used together.

DETAILED DESCRIPTION OF THE INVENTION

The bis-biguanide compounds of this invention have the generic formula:

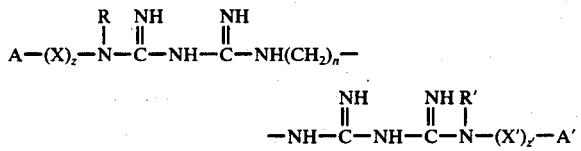

wherein A and A' each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ may optionally be interrupted by oxygen or sulfur atoms, aromatic nuclei, etc.

The salts of the above compounds are especially desirable. Water-insoluble salts are disclosed in the copending application of John W. Haefele, having Ser. No. 635,030, filed Nov. 25, 1975 and in Haefele, U.S. Pat. No. 3,934,002, issued Jan. 20, 1976. The Haefele application and patent are incorporated herein by reference. Water-insoluble salts for the purpose of this invention are those having a solubility in 25° C. water of less than about 0.04%.

The water-soluble salts of the bis-biguanides are the most preferred and most desirable materials since it is then possible to form clear solution compositions. Suitable water-soluble salts include the acetate, the hydrochloride, and especially the gluconate salts of the above compounds. Water-soluble salts for the purpose of this invention are those having a solubility in 25° C. water equal to or greater than about 0.04%. Specific examples of these bis-biguanide compounds are disclosed hereinafter.

The above compounds are effective antiplaque agents which demonstrate anticaries activity. However, when compositions containing these compounds are used continuously in a program of oral hygiene, a rather offensive brown stain forms on the oral surfaces which is resistant to removal by ordinary brushing with conventional dentifrices. This stain problem prevents compositions containing these bis-biguanide compounds from being accepted by the consumer. The bis-biguanide compounds are normally used in amounts of from about 0.01% to about 2.5% by weight of the composition, preferably from about 0.05% to about 1.2%, and most preferably from about 0.1% to about 0.8%. Depending upon the composition, lesser or greater amounts may be used. In general, all that is required is to have an effective amount of the bis-biguanide salt in the mouth sufficient to give antiplaque and/or anticaries effectiveness.

The specific amino carboxylate compounds which have been found to be effective in preventing stain, but which do not precipitate the bis-biguanide compound are ethylenediaminediacetic acid (EDDA) and its pharmaceutically acceptable water-soluble salts (i.e., salts being soluble to the extent of equal to or greater than 0.04% by weight in 25° C. water). Examples of pharmaceutically acceptable water-soluble salts of EDDA are sodium, potassium and ammonium salts. Mixtures of these amino carboxylate compounds can also be used. The EDDA or salts thereof can be either symmetrical or unsymmetrical. The symmetrical compounds, are preferred, and are the ones used in the working examples hereinafter. EDDA has relatively low chelating potential for calcium and is therefore safer for use in the mouth than the amino carboxylate compounds disclosed in Haefele, U.S. Pat. No. 3,937,807, issued Feb. 10, 1976. Similar amino carboxylates, including ethylenediaminetetraacetic acid and iminodiacetic acid, precipitate the bis-biguanide compound and are very damaging to tooth enamel.

Within the pH range of the oral compositions of the present invention, it is to be understood that the chelator compounds react with the bis-biguanide compounds in the ratio of two moles of chelator to one mole of bisbiguanide compound. Enough chelator should be present in the oral compositions herein such that some excess chelator is present in addition to that which reacts or would react with the bis-biguanide present. The concentration of such excess chelator generally ranges from about 0.01% to 1.25%, preferably from about 0.1% to about 1.0% by weight of the composition.

The pH of the compositions of this invention is preferably maintained within the range of from about 4.5 to about 9.5, more preferably from about 6.5 to about 7.5. Below about 4.5, damage to dental enamel can occur. Above about 9.5, the alkalinity becomes cosmetically undersirable and may irritate soft tissue in the mouth. The pH of the compositions of the invention can be adjusted if necessary, by commonly used acidifying agents such as acetic acid, gluconic acid, etc., or alkalizing agents such as sodium hydroxide, potassium hydroxide, etc.

In addition to the essential bis-biguanide and chelator components of the oral compositions of this invention as described in the foregoing, such compositions can also contain carriers suitable for use in the oral cavity. Such carriers include the usual components of toothpastes, toothpowders, mouthwashes, prophylaxis pastes and the like as more fully described hereinafter.

Preferred oral composition embodiments of the present invention are dentifrice compositions, especially toothpastes. Dentifrices preferably contain from about 0.1% to 2.0% by weight of the bis-biguanide component and from about 0.1% to 1.25% by weight of the chelator in excess of that which reacts with the bis-biguanide. Dentifrices also contain an abrasive polishing material and typically also contain sudsing agents, flavoring agents and sweetening agents. Toothpaste compositions additionally contain binders, humectants and water.

The dentifrice abrasive, generally has a particle size of from about 0.1 to about 10 microns in diameter and can be any abrasive polishing material which does not excessively abrade toothe dentin. These include, for example, calcium carbonate, dicalcium orthophosphate dihydrate, calcium pyrophosphate, calcium polymetaphosphate and insoluble sodium polymetaphosphate. Preferably, however, the abrasive is one which has a high degree of compatibility with the bis-biguanides. These include, for example, silica xerogels such as those described in U.S. Pat. No. 3,538,230 to Pader et al., issued Nov. 3, 1970; hydrofluoric acid-treated amorphous silica abrasives such as those disclosed in U.S. Pat. No. 3,862,307 to DiGiulio, issued Jan. 21, 1975; mineral abrasives coated with cationic polymers such as those disclosed by J. J. Benedict in USSCRNO. 471,941, filed May 21, 1974; and condensation products of urea and formaldehyde such as those disclosed by Cooley et al., in U.S. Pat. No. 3,070,510, issued Dec. 25, 1972.

The total amount of abrasive materials in the dentifrice embodiments of this invention can range from about 0.5% to about 95% by weight of the dentifrice. Preferably toothpastes contain from about 6% to about 60% by weight and toothpowders contain from about 20% to about 95% by weight abrasives.

Dentifrice compositions can also contain sudsing agents. Suitable sudsing agents are those which are reasonably stable and form suds throughout a wide pH range, and which will not react with the bis-biguanide compound, i.e., non-soap nonionic, cationic, zqitterionic and amphoteric organic synthetic detergents.

The nonionic synthetic detergents which can be used with the oral compositions of the present invention may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water-insolubility has a molecular weight of from about 1,500 to about 1,800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide with ethylene diamine — products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxides per mole of coconut alcohol, the coconut alcohol fraction having from 10 to 14 carbon atoms.

4. Long chain tertiary amine oxides corresponding to the following general formula:

$$R_1R_2R_3N \rightarrow O,$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formulas:

$$RR'R''P \rightarrow 0$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semi-polar bond. Examples of suitable phosphine oxides are: dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)-phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxy propyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

The zwitterionic synthetic detergents useful in the oral compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2-Y^{(+)}-\underset{\underset{(R^3)_x}{|}}{CH_2}-R^4-Z^{(-)}$$

wherein $R^2$ contains an alkyl, alkenyl, or hydroxy alkyl radical of from about 8 to about 18 carbon atoms from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; x is 1 when Y is a sulfur atom and 2 when Y is a nitrogen or phosphorus atom; $R^4$ is an alkylene or hydroxyalkylene of from 1 to 4 carbon atoms; and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate; pl 3-[P,P-diethyl-P-

3,6,9-trioxatetradecoxylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate; p1 3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

The cationic synthetic detergents useful in the oral compositions of the present invention can be broadly defined as quaternary ammonium compounds having 1 long alkyl chain containing from about 8 to about 18 carbon atoms such as lauryl trimethylammonium chloride; cetyl pyridinium chloride; cetyl trimethylammonium bromide; di-isobutylphenoxyethoxyethyldimethylbenzylammonium chloride; coconutalkyltrimethylammonium nitrite; cetyl pyridinium fluoride; etc. Especially preferred are the quaternary ammonium fluorides described in U.S. Pat. No. 3,535,421, Briner et al., issued Oct. 20, 1970, incorporated by reference hereinbefore, where said quaternary ammonium fluorides have detergent properties.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of compounds falling within this definition are sodium 3-dodecylaminopropionate, sodium 3-dodecylaminopropane sulfonate, dodecyl-beta-alanine, N-alkyl-taurines such as the one prepared by reacting dodecylamine with sodium isethionate according to the teaching of U.S. Pat. No. 2,658,072, Kosmin, Nov. 3, 1953, N-higher alkyl aspartic acids such as those produced according to the teaching of U.S. Pat. No. 2,438,091 Lynch, Mar. 16, 1948, and the products sold under the trade name "Miranol" and described in U.S. Pat. No. 2,528,378, Mannheimer, Oct. 31, 1950. The sudsing agent can be present in the dentifrice compositions of this invention in an amount from 0.5% to 5% by weight of the total compositions.

It is preferable to have a water-soluble fluoride compound present in dentifrices in an amount sufficient to give a fluoride concentration of from about 0.0025% to about 5.0% by weight, preferably from about 0.005% to about 2.0% by weight, to provide additional anticaries effectiveness. Suitable fluoride sources are disclosed in the examples given hereinafter. Preferred fluorides are sodium fluoride, stannous fluoride, indium fluoride, and sodium monofluorophosphate. Norris et al, U.S. Pat. No. 2,946,725, issued July 26, 1960; Widder et al, U.S. Pat. No. 3,678,154, issued July 18, 1972 Agricola et al, U.S. Pat. application Ser. No. 501,909, filed Aug. 30, 1974, now U.S. Pat. No. 3,959,458, issued May 25, 1976 disclose dentifrice compositions containing fluoride sources and are incorporated herein by reference.

In preparing toothpastes, it is necessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Flavoring agents can also be added to dentifrice compositions. Suitable flavoring agents include oil of wintergreen, oil of peppermint, oil of spearmint, oil of sassafras, and oil of clove. Sweetening agents which can be used include saccharin, dextrose, levulose and sodium cyclamate. Flavoring agents are generally used in dentifrices at levels of from about 0.01% to 2% by weight and sweetening agents at levels of from about 0.05% to about 2% by weight.

Another type of preferred embodiment of the instant invention is a mouthwash composition. Conventional mouthwash composition components can comprise the carrier for the bis-biguanides and chelators of the present invention. Mouthwashes generally comprise a water/ethyl alcohol solution and preferably other ingredients such as flavor, sweeteners, humectants and sudsing agents such as those mentioned above for dentifrices. The humectants, such as glycerine and sorbitol give a moist feel to the mouth. Generally, on a weight basis the mouthwashes of the invention comprise 5% to 60% (preferably 10% to 25%)ethyl alcohol, 0% to 20% (preferably 5% to 20%) glycerine or other humectant, 0% to 2% (preferably 0.1% to 1.5%) sudsing agent, 0% to 0.5% (preferably 0.05% to 0.5%) sweetening agent such as saccharin and 0% to 0.3% (preferably 0.05% to 0.3%) flavoring agent, and the balance water. The amount of bis-biguanide antibacterial agent in mouthwashes is typically from about 0.01% to about 1.2% by weight.

In addition to the bis-biguanides, chelating and carrier components of this invention, it is possible to include a phosphorus-containing anticalculus agent as disclosed in Haefele, U.S. Pat. No. 3,934,002, issued Jan. 20, 1976. This patent is incorporated herein by reference. However, if a solution is desired containing water-soluble bis-biguanide salt, then the phosphorus-containing anticalculus agent should not be used since it will form an insoluble salt with the bis-biguanide compound.

In its method aspect, the present invention comprises a method of reducing dental plaque and/or caries by applying to the oral cavity an effective amount of a composition of the invention. Any amount which is sufficient to achieve the desired reduction is an effective amount. Generally, an amount which supplies at least about 0.001 g. per usage of the bis-biguanide compound is effective. Composition components can be utilized in the instant method in sequential fashion instead of as single homogenous compositions.

Several representative oral compositions illustrating this invention are set forth in the following examples.

EXAMPLE I

A solution is prepared containing 0.2 gram chlorhexidine [1,6-di-(N$^5$-p-chlorophenyl-N$^1$-diguanido)hexane] digluconate; 1.0 gram ethylenediaminediacetic acid (EDDA); 2.7 g. 2N sodium hydroxide solution; and 96.1 grams water, said solution having a pH of about 7.0. No precipitate forms. The resulting clear composition, when used in the mouth, inhibits the formation of plaque, calculus, caries and gingivitis, but with continued use, does not form the large amount of stain that would result if the EDDA was not present.

EXAMPLE II 0.025 gram sodium fluoride was added to 100 grams of the solution of Example I. This solution inhibits the formation of plaque and calculus, and in addition, has greater anticaries effectiveness.

EXAMPLE III

A solution is prepared containing 0.2 gram chlorhexidine digluconate; 1.0 gram EDDA; 1.0 gram polyoxyethylene (20) sorbitan monolaurate; 2.7 grams 2N sodium hydroxide solution; and 95.1 grams water. The solution has a pH of about 7.0. This solution, when used in the mouth on a regular basis, inhibits the formation of plaque, calculus and caries without excessive stain formation.

Several mouthwash compositions illustrating this invention are set forth in the following examples.

| Component | Ex. | Percent by Weight | | | | |
|---|---|---|---|---|---|---|
| | | IV | V | VI | VII | VIII |
| Glycerine | | 10.0 | 10.0 | 10.0 | 10.0 | 10.0 |
| Ethyl alcohol | | 16.5 | 16.5 | 16.5 | 16.5 | 16.5 |
| Polyoxyethylene (20) sorbitan monoisostearate | | 1.00 | 1.00 | 1.00 | 1.50 | 0.5 |
| Sodium saccharin | | .045 | .045 | .045 | .045 | .045 |
| Chlorhexidine digluconate | | 0.1 | 0.15 | 0.15 | 0.15 | 0.20 |
| Flavor | | .088 | .088 | .088 | .088 | .088 |
| Dipotassium EDDA | | 0.5 | | | | |
| Disodium EDDA | | | 0.9 | | | |
| Diammonium EDDA | | | | 0.9 | | |
| Stannous EDDA | | | | | 0.9 | |
| Sodium fluoride | | | | | | 0.10 |
| Water | | | | balance | | |

Adjust pH to 7.

EXAMPLE IX

A toothpowder which constitutes yet another embodiment of this invention has the following formulation:

| Component | Percent by Weight |
|---|---|
| Calcium pyrophosphate | 92.30 |
| Polyoxyethylene (20) sorbitan monolaurate | 2.30 |
| Sodium saccharin | 0.25 |
| Flavoring | 1.45 |
| Chlorhexidine diacetate | 0.70 |
| Disodium EDDA | 3.00 |

When diluted with water and brushed upon the teeth in the conventional manner, this composition has a pH of approximately 7.0. The composition retards the formation of plaque, calculus, and caries without excessive staining.

EXAMPLE X

A prophylaxis paste for use in the dental office for removal of stains and polishing the tooth surface after mechanical removal of calculus is formulated as follows:

| Component | Percent by Weight |
|---|---|
| Composition A: | |
| Navajo pumice | 67.1 |
| TiO$_2$ | 4.0 |
| Glycerine | 15.352 |
| Hydroxyethylcellulose | .222 |
| Sodium saccharin | .326 |
| Glycine fluoride | 1.0 |
| Disodium EDDA | 12.0 |
| Composition B: | |
| Chlorhexidine digluconate | 2.7 |
| Water | 97.30 |

Immediately prior to use, 5.5 gm. of composition A are mixed with 5.5 gm. of Composition B to attain the desired texture and adjusted to pH 7.0. Total chelator concentration in the paste mixture thus amounts to 6.0%. The paste is then applied to the tooth surfaces with a rubber prophylactic cup in the conventional manner. This composition inhibits the formation of plaque, calculus, and caries without adverse effects of stain formation.

EXAMPLE XI

A toothpaste prepared in accordance with this invention has the following composition:

| Component | Percent by Weight |
|---|---|
| Precipitated urea/formaldehyde condensate (abrasive) | 31.00 |
| Sorbitol (70% aqueous solution) | 6.25 |
| Glycerine | 18.00 |
| Polyoxyethylene sorbitan (20) monoisostearate | 1.50 |
| Hydroxyethylcellulose | 1.15 |
| Magnesium aluminum silicate | 0.40 |
| Sodium saccharin | 0.04 |
| Flavoring | 0.95 |
| Disodium ethane-1-hydroxy-1,1-diphosphonate | 0.50 |
| Dipotassium EDDA | 4.0 |
| Sodium monofluorophosphate | 3.00 |
| Sodium fluoride | 0.03 |
| Chlorhexidine digluconate | 0.80 |
| Water | balance |

Mole ratio polyphosphonate/fluoride about 2.4. pH adjusted to 7.5 with 5N NaOH.

This composition is effective in retarding the formation of dental calculus when used in a conventional manner. This composition also inhibits plaque and caries.

EXAMPLE XII

A mouthwash of the present invention is prepared according to the following formula:

| Component | Percent by Weight |
|---|---|
| Chlorhexidine digluconate | 0.20 |
| EDDA | 0.9 |
| Polyoxyethylene sorbitan (20) monoisostearate | 1.0 |
| Ethanol | 12.0 |
| Sodium saccharin | 0.045 |
| Glycerol | 6.0 |
| Flavor | 0.08 |
| Water | balance | pH adjusted to 7.0 with 2N sodium hydroxide

EXAMPLE XIII

Oral surfaces are treated sequentially with a 0.2% aqueous solution of chlorhexidine digluconate and a 1% aqueous solution of disodium EDDA containing 0.25% sodium fluoride.

When in the above examples the following watersoluble fluoride agents are substituted, either wholly or in part, for the sodium fluoride, substantially equivalent results are obtained in that the formulas provide additional anticaries activity: Sodium monofluorophosphate, stannous fluoride, potassium fluoride, lithium fluoride, cesium fluoride, ammonium fluoride, indium fluoride, stannous fluorizirconate, lead fluoride, palladium fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine hydrofluoride, diethylaminoethyloctoylamide hydrofluoride, diethanolaminoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride, $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N'-dilaurylethylene-diammonium difluoride, N-cetylpyridinium fluoride, N:n-dilauryl-morpholinium fluoride, N-myristyl-N-ethylmorpholinium fluoride, N-(octylaminocarbonylethyl)-N-benzyl-dimethylammonium fluoride, N-(β-hydroxydodecyl)trimethylammonium fluoride, N-phenyl-N-hexadecyldiethylammonium fluoride, N-cyclohexyl-N-octadecyl-dimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-eicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, and mixtures thereof in, e.g., 1:1 proportions. The glycine fluorides are preferred.

When in the above examples the following surfaceactive agents are inserted in an amount of from about 1 to 2% as an additional ingredient, substantially equivalent results are obtained, except that the compositions have enhanced detergency effects: Polypropylene glycol (M.W. 1700) polyoxyethylene (M.W. 1500); polyoxypropylene (70) ethylenediamine polyoxyethylene (100); coconut alcohol polyoxyethylene (20); dimethyldodecylamine oxide; oleyldi(2-hydroxyethyl)amine oxide; dimethyloctylamine oxide; dimethyldecylamine oxide; dimethyltetradecylamine oxide; 3,6,9-trioxaheptadecyldiethylamine oxide; di(2-hydroxyethyl)-tetradecylamine oxide; 2-dodecoxyethyldimethylamine oxide; 3-dodecoxy-2-hydroxypropyldi(3-hydroxypropyl)amine oxide; dimethylhexadecylamine oxide; tetradecyldimethylphosphine oxide; tetradecyldimethylphosphine oxide; tetradecylmethylethylphosphine oxide; 3,6,9-trioxaoctadecyldimethylphosphine oxide; cetyldimethylphosphine oxide; 3-dodecoxy-2-hydroxypropyldi(2-hydroxyethyl)phosphine oxide; stearyldimethylphosphine oxide; cetylethylpropylphosphine oxide; oleyldiethylphosphine oxide; dodecyldiethylphosphine oxide; tetradecyldiethylphosphine oxide; dodecyldipropylphosphine oxide; dodecyldi(hydroxymethyl)phosphine oxide; dodecyldi(2-hydroxyethyl)phosphine oxide; tetradecylmethyl-2-hydroxypropylphosphine oxide; oleyldimethylphosphine oxide; 2-hydroxydodecyldimethylphosphine oxide; octadecyl methyl sulfoxide; 2-ketotridecyl methyl sulfoxide; 3,6,9-trioxaoctadecyl 2-hydroxyethyl sulfoxide; dodecyl methyl sulfoxide; oleyl 3-hydroxypropyl sulfoxide; tetradecyl methyl sulfoxide; 3-methoxytridecyl methyl sulfoxide; 3-hydroxytridecyl methyl sulfoxide; 3-hydroxy-4-dodecoxybutyl methylsulfoxide; 4-(N,N-di(2-hydroxyethyl)-N-octadecylammonio]-butane-1-carboxylate; 5-(S-3-hydroxypropyl-S-hexadecylsulfonio]-3-hydroxypentane-1-sulfate; 3-[P,P-diethyl-P-3,6,9-trioxatetradecoxylphosphonio]-2-hydroxypropane-1-phosphate; 3-[N,N-dipropyl-N-3-dodecoxy-2-hydroxypropylammonio]-propane-1-phosphonate; 3-(N,N-dimethyl-N-hexadecylammonio)propane-1-sulfonate; 3-(N,N-dimethyl-N-hexadecylammonio)-2-hydroxypropane-1-sulfonate; 4-[N,N-di(2-hydroxyethyl)-N-(2-hydroxydodecyl) ammonia]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; 5-[N,N-di(3-hydroxypropyl)-N-hexadecylammonio]-2-hydroxypentane-1-sulfate; dodecyltrimethylammonium chloride; nonylbenzylethyldimethylammonium nitrate; tetradecylpyridinium bromide; octadecylbutylpropylmethylphosphonium nitrite; decyldimethylsulfonium chloride; (hexylphenyl)dimethylbenzylammonium fluoride; eicosyldimethylbenzylphosphonium chloride; coconutalkyldimethylbenzylmethylmorpholinium nitrate; octadecylmethylbenzylsulfonium sulfate; laurylpyridinium chloride; laurylpyridinium bromide; laurylpyridinium bisulfate; laurylpyridinium-5-chloro-2-mercaptobenzothiazole; laurylpicolinium-p-toluenesulfonate; tetradecylpyridinium bromide; cetylpyridinium chloride; cetylpyridinium bromide; laurylisoquinolinium bromide; laurylisoquinolinium saccharinate; alkylisoquinolinium bromide; N-cetyl-N-ethyl-morpholinium ethosulfate; benzalkonium chloride; monoquaternaries $R_4N^+X^-$ (one R group is fatty); octadecyltrimethylammonium chloride; coconut alkyl trimethylammonium chloride; dodecylbenzyltri (octyldecyl)ammonium chloride; monoquaternaries $R_4N^+X^-$ (two R groups are fatty); dihexadecyldimethylammonium chloride; dicoconut alkyl dimethylammoniumchloride; monoquaternaries R₄N⁺X (three R groups are fatty); tri(hydrogenated tallow) methylammonium chloride; distilled tallow amine acetate; diamine acetates; N-oleyl propylene diamine monoacetate; condensation product of octyl phenol with 15 moles of ethylene oxide per mole of octyl phenol; dimethyldodecylamine oxide; dodecyldimethylphosphine oxide; tetradecyl methyl sulfoxide; 3-(N,N-dimethyl-N-hexadecylammonio)propane-1-sulfonate; 3-dodecylaminopropionate; and dodecyl-beta-alanine.

When in the above examples, the following bis-biguanide compounds are substituted, either wholly or in part (50%) for the preferred chlorhexidine digluconate, substantially equivalent results are obtained in that plaque, calculus, caries and gingivitis are inhibited with reduced staining as compared to the use of the bis-biguanide compounds alone: 1,6-bis-(3-ethylhexylbiguanidohexane)dihydrochloride; 1,6-di-(N⁵-phenyl-N₁-diguanido)-hexane tetrahydrochloride; 1,6-di-(N₅-phenyl-N₅-methyl-N¹-diguanido)hexane dihydrochloride; 1,6-di-(N⁵-o-chlorophenyl-N¹-diguanido)hexane dihydrochloride; 1,6-di-(N⁵-2,6-dichlorophenyl-N¹-diguanido)-hexane dihydrochloride; 1,6-di-(N⁵-p-methoxyphenyl-N¹-diguanido)hexane dihydrochloride; 1,6-di-(N⁵-p-nitrophenyl-N¹-diguanido)hexane dihydrochloride; ω,ω'-di-(N⁵-phenyl-N¹-diguanido)-di-n-propylether dihydrochloride; ω, ω'-di-(N⁵-p-chlorophenyl-N¹-diguanido)-di-n-propylether tetrahydrochloride; 1,6-di-(N⁵-2,4-dichlorophenyl-N¹-diguanido)hexane tetrahydrochloride; 1,6-di-(N⁵-p-methylphenyl-N¹-diguanido) hexane dihydrochloride; 1,6-di-(N⁵-2,4,5-trichlorophenyl-N¹-diguanido)hexane tetrahydrochloride; 1,6-di-[N⁵-alpha(p-chlorophenyl)ethyl-N¹-diguanido] hexane dihydrochloride; ω,ω'-di-(N⁵-p-chlorophenyl-N¹-diguanido)m-xylene dihydrochloride; 1,12-di-(N⁵-p-chlorophenyl-N¹-diguanido) dodecane dihydrochloride; 1,10-di-(N⁵-phenyl-N¹-diguanido) decane tetrahydrochloride; 1,12-di-(N⁵-phenyl-N¹-diguanido) dodecane tetrahydrochloride; 1,6-di-(N⁵-p-chlorophenyl-N¹-diguanido)hexane tetrahydrochloride; ethylene bis(1-tolyl biguanide); ethylene bis(p-tolyl biguanide); ethylene bis(3,5-dimethylphenyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis(N-butylphenyl biguanide); ethylene bis(2,5-diethoxyphenyl biguanide); ethylene bis(2,4-dimethylphenyl biguanide); ethylene bis(o-diphenyl biguanide); ethylene bis(mixed amyl naphthyl biguanide); N-butyl ethylene bis(phenyl biguanide); trimethylene bis(o-tolyl biguanide); N-butyl trimethylene bis(phenyl biguanide); tetramethylene bis(1-tolyl biguanide); the specific compounds disclosed in U.S. Pat. No. 2,863,919, Burtwell et al., Dec. 9, 1958), said patent being incorporated herein by reference; the specific compounds disclosed in U.S. Pat. No. 3,468,898, Cutler et al., (Sept. 23, 1969), said patent being incorporated herein by reference; and the corresponding pharmaceutically acceptable salts of all of the above such as the acetates; gluconates; hydrochlorides; hydrobromides; citrates, bisulfites, fluorides; polymaleates; N-coconut alkyl sarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; perfluoropropionates; and the salts prepared by reacting the following salts with the bis-biguanide compounds: Disodium ethane-1-hydroxy-1,1-diphosphonate; disodium salt of ethane-1,2-dicarboxy-1,2-diphosphonic acid; dipotassium salt of ethane-1,2-dicarboxy-1,2-dihydroxy-1,2-diphosphonic acid; the monocalcium salt of ethene-1,2-dicarboxy-1-phosphonic acid; the monomagnesium salt of ethane-1,2-dicarboxy-1-hydroxy-1,1-diphosphonic acid; the di(triethanolammonium) salt of ethane-1,2-dicarboxy-1,2-diphosphonic acid; the disodium salt of ethane-1,2-dicarboxy-1,2-diphosphonic acid; diammonium salt of ethane-1,2-dicarboxy-1,2-diphosphonic acid; monocalcium salt of ethane-1,2-dicarboxy-1,2-dihydroxy-1,2-diphosphonic acid; distannous salt of ethane-1,2-dicarboxy-1-hydroxy-1,2-diphosphonic acid; indium salt of ethene-1,2-dicarboxy-1-phosphonic acid; triammonium salt of ethane-1, 2-dicarboxy-1,2-dihydroxy-1,2-diphosphonic acid; trisodium salt of ethene-1,2-dicarboxy-1-phosphonic acid; distannous salt of ethane-1,2-dicarboxy-1,2-diphosphonic acid; hexasodium salt of cyclic tetraphosphonic acid; trisodium salt of methanecyclohexylhydroxydiphosphonic acid; diammonium salt of methanecyclobutylhydroxydiphosphonic acid; monocalcium salt of methanecyclopentylhydroxydiphosphonic acid; distannous salt of methanecycloheptylhydroxydiphosphonic acid; indium salt of methanecyclooctylhydroxydiphosphonic acid; triammonium salt of methanecyclononylhydroxydiphosphonic acid; trisodium salt of methanecyclodecylhydroxydiphosphonic acid; distannous salt of methanecyclohexylhydroxydiphosphonic acid; methanecycloalkylhydroxydiphosphonic acid; tris(1-phosphonoethyl)amine; tetrasodium salt of tris(2-phosphono-2-propyl)amine; dipotassium salt of bis(phosphonomethyl(-1-phosphonoethyl amine; monocalcium salt of bis(phosphonomethyl)-2-phosphono-2-propyl amine; monomagnesium salt of bis(1-phosphonoethyl)phosphonomethyl amine; distannous salt of bis(2-phosphono-2-propyl)phosphonomethyl amine; Victamide and mixtures thereof, e.g., 1:1 and 1:1:1 ratios.

What is claimed is:
1. An oral composition effective in inhibiting bis-biguanide tooth staining and the formation of plaque, caries and calculus comprising a carrier suitable for use in the oral cavity and
  A. from about 0.01% to about 2.5% by weight of a tooth staining bis-biguanide compound, otherwise tending to produce a rather offensive brown tooth stain upon continuous oral use and having the generic formula:

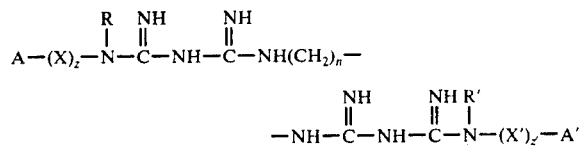

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms;

wherein n is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof; and B. from about 0.10% to about 1.25% by weight of the composition of a chelator in excess of the amount of chelator which will react with the bis-biguanide compounds, and which in said concentration range effectively reduces said bis-biguanide tooth stain without precipitating said tooth-staining bis-biguanide, said chelator being an amino carboxylate compound selected from the group consisting of: Ethylene-diaminediacetic acid and the water-soluble pharmaceutically acceptable salts thereof, said composition having a pH of from about 4.5 to about 9.5.

2. The composition of claim 1 wherein the bis-biguanide compound is a water-soluble salt and the ethylenediaminediacetic acid or salt thereof is symmetrical.

3. The composition of claim 2 wherein the pH is from about 6.5 to about 7.5.

4. The composition of claim 2 containing a water-soluble source of fluoride in a quantity sufficient to provide fluoride in an amount of from about 0.0025% to about 5.0% by weight as $F^-$.

5. The composition of claim 2 containing from about 0.05% to about 1.2% by weight of the bis-biguanide compound and from about 0.1% to about 1% by weight of the amino carboxylate compound.

6. The composition of claim 2 wherein the bis-biguanide compound is [1,6-di-($N^5$-p-chlorophenyl-$N^1$-diguanido)hexane] digluconate.

7. The composition of claim 2 wherein the bis-biguanide compound is present as a pharmaceutically acceptable salt selected from the group consisting of the hydrochloride, acetate, and gluconate salts.

8. The composition of claim 2 wherein $A - (X)_z$ is an ethylhexyl group and n is 6.

9. The composition of claim 2 wherein A and A' are each p-chlorophenyl groups, z and z' are 0, and n is 6.

10. The composition of claim 2 in the form of a dentifrice
A. wherein the bis-biguanide compound comprises from about 0.1% to 2.0% by weight of the composition; and
B. wherein the carrier component comprises an abrasive polishing agent present to the extent of from about 0.5% to about 95% by weight of said composition.

11. The composition of claim 10 wherein the abrasive is selected from the group consisting of silica xerogels, hydrofluoric acid-treated amorphous silica, mineral abrasives coated with cationic polymers and condensation products of urea and formaldehyde.

12. The composition of claim 11 wherein the bis-biguanide is [1,6-di-($N^5$-p-chlorophenyl-$N^1$-diguanido)hexane].

13. The composition of claim 2 in the form of a mouthwash wherein the bis-biguanide component comprises from about 0.01% to 1.2% by weight of the composition and wherein the carrier component comprises water and an additional ingredient selected from the group consisting of
A. from about 5% to about 60% by weight of the composition of ethanol;

B. from about 5% to about 20% by weight of the composition of glycerine;
C. from about 0.1% to about 1.5% by weight of the composition of a nonsoap, nonionic, cationic, zwitterionic or amphoteric sudsing agent;
D. from about 0.05% to about 0.5% by weight of the composition of sweetening agent;
E. from about 0.05% to about 0.3% by weight of the compositions of flavoring agent; and
F. mixtures thereof.

14. The composition of claim 13 wherein the bis-biguanide is [1,6-di-($N^5$-p-chlorophenyl-$N^1$-diguanido)hexane].

15. The process of inhibiting bis-biguanide tooth-staining and dental plaque and caries, comprising the steps of:

A. contacting the oral cavity with an effective amount of a composition comprising a carrier suitable for use in the oral cavity, and from about 0.01% to about 2.5% by weight of a tooth-staining bis-biguanide compound, otherwise tending to produce a rather offensive brown tooth stain upon continuous oral use, and having a generic formula:

$$A-(X)_z-N-\overset{R}{\underset{|}{}}\overset{NH}{\underset{\|}{C}}-NH-\overset{NH}{\underset{\|}{C}}-NH(CH_2)_n-$$

$$-NH-\overset{NH}{\underset{\|}{C}}-NH-\overset{NH}{\underset{\|}{C}}-\overset{R'}{\underset{|}{N}}-(X')_z-A$$

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof; and B. contacting said oral cavity with a second composition comprising a carrier suitable for use in the oral cavity and from about 0.10% to about 1.25% by weight of the combined compositions of a chelator in excess of the amount of chelator which will react with the bis-biguanide compounds of Step A, and which in said concentration range effectively reduces said bis-biguanide tooth stain without precipitating said tooth-staining bis-biguanide, said chelator being an amino carboxylate compound selected from the group consisting of: Ethylenediaminediacetic acid, and the water-soluble pharmaceutically acceptable salts thereof, said compositions having a pH of from about 4.5 to about 9.5.

16. A process of inhibiting bis-biguanide tooth-staining and dental plaque and caries comprising the step of contacting the oral cavity with an effective amount of a composition comprising a carrier suitable for use in the oral cavity; and A. from about 0.01% to about 2.5% by weight of a tooth-staining bis-biguanide compound, otherwise tending to produce a rather offensive brown tooth stain upon continuous oral use, and having the generic formula:

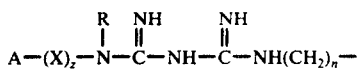

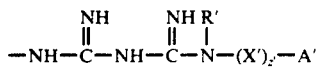

wherein A and A' each represent either (1) a phenyl radical which can contain as substituents up to two alkyl or alkoxy groups containing from 1 [t-] to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl, or naphthyl moieties, or the pharmaceutically acceptable salts thereof; and B. from about 0.10% to about 1.25% by weight of the composition of a chelator in excess of the amount of chelator which will react with the bis-biguanide compounds, and which in said concentration range effectively reduces said bis-biguanide tooth stain without precipitating said tooth-staining bis-biguanide, said chelator being an amino carboxylate compound selected from the group consisting of: Ethylene-diaminediacetic acid, and the water-soluble pharmaceutically acceptable water-soluble salts thereof, said composition having a pH of from about 4.5 to about 9.5.

17. The process of claim 16 wherein the bis-biguanide compound is a water-soluble salt of 1,6-di-($N^5$-p-chlorophenyl-$N^1$-diguanido)hexane.

18. The process of claim 17 wherein the salt of 1,6-di-($N^5$-p-chlorophenyl-$N^1$-diguanido)hexane is selected from the group consisting of the hydrochloride, acetate and gluconate salts.

19. An oral composition effective in inhibiting bis-biguanide tooth staining and the formation of plaque, caries and calculus comprising a carrier suitable for use in the oral cavity and A. from about 0.01% to about 2.5% by weight of a tooth staining bis-biguanide compound, otherwise tending to produce a rather offensive brown tooth stain upon continuous oral use and having the generic formula:

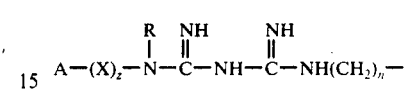

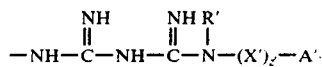

wherein A and A' each represent either (1) a phenyl radical which can contain as substituents up to two alkyl or alkoxy groups containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein z and z' each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ can be interrupted by up to 5 ether, thioether, phenyl, or naphthyl moieties; or the pharmaceutically acceptable salts thereof; and B. from about 0.5% to about 6.0% by weight of the composition of a chelator which in said concentration range is present in excess of the amount of chelator which will react with the bis-biguanide and which effectively reduces said bis-biguanide tooth stain without precipitating said tooth-staining bis-biguanide, said chelator being an amino carboxylate compound selected from the group consisting of: Ethylene-diaminediacetic acid and the water-soluble pharmaceutically acceptable salts thereof, said composition having a pH of from about 4.5 to about 9.5.

20. A composition in accordance with claim 19 wherein the bis-biguanide is a water-soluble chlorhexidine salt.

* * * * *